United States Patent [19]

Carden

[11] Patent Number: 5,494,048
[45] Date of Patent: Feb. 27, 1996

[54] ANESTHETIST'S PYLON

[76] Inventor: Edward Carden, 4 Jib St., Unit 14, Marina Del Rey, Calif. 90292

[21] Appl. No.: 161,289

[22] Filed: Dec. 3, 1993

Related U.S. Application Data

[63] Continuation-in-part of Ser. No. 999,611, Dec. 31, 1992, abandoned.

[51] Int. Cl.⁶ .......................... A61G 15/00; A61F 11/06; A61F 5/00
[52] U.S. Cl. .......................... 128/845; 128/876; 602/32
[58] Field of Search .......................... 602/32–36, 38–40; 128/876, 845, 846; 24/67.7, 67.9

[56] References Cited

U.S. PATENT DOCUMENTS

| | | | |
|---|---|---|---|
| 1,004,392 | 9/1911 | Ehrlich | 24/67.7 |
| 2,658,506 | 11/1953 | Haskell | 602/32 |
| 2,831,482 | 4/1958 | Cobb | 602/33 |
| 2,940,442 | 6/1960 | Wilhelm | 602/32 |
| 3,121,388 | 2/1964 | Benson | 24/67.7 |
| 3,276,444 | 10/1966 | Rice | 602/32 |
| 3,390,675 | 7/1968 | Giannestras | 602/33 |
| 3,596,655 | 8/1971 | Corcoran | 602/32 |
| 4,532,680 | 8/1985 | Hashimoto | 24/67.9 |
| 4,538,598 | 9/1985 | Gill | 602/33 |
| 5,147,287 | 9/1992 | Jewell | 602/32 |

*Primary Examiner*—Michael A. Brown
*Attorney, Agent, or Firm*—Christie, Parker & Hale

[57] ABSTRACT

A chin support holds an anesthetized patient's head in the proper position during surgery so that the unconscious patient's airway is held open. A pylon attaches to and extends up from the side of an operating table. A tether attaches to the top of the pylon and extends around the patient's chin to keep the patient's head tilted during surgery. The pylon is held in place against the operating table by the tension on the tether when the chin support is in use.

13 Claims, 9 Drawing Sheets

ANESTHETIST'S PYLON

This application is a CIP of Ser. No. 07/999,611, filed Dec. 31, 1992, now abandoned.

FIELD OF THE INVENTION

The present invention relates to a device to be used during surgery for holding an anesthetized patient's head in a position to maintain an open airway during the surgery.

BACKGROUND OF THE INVENTION

During surgery it is important that an anesthetized patient's airway remain open. Normally, the anesthetist, a member of the surgical team, uses one hand to physically hold the patient's head in a position which will insure that the airway is maintained in an open condition. The airway is most easily kept in an open condition by tilting the patient's head backward by pulling the patient's chin up and away from the patient's body.

During long surgeries, reliance on this practice very often is fatiguing to the anesthetist, and it can severely restrict his or her ability to move about and attend to other matters. If the anesthetist is required to perform any function requiring the use of both hands, then another member of the surgical staff must temporarily hold the patient's head in order to maintain the airway.

While anesthetists sometimes use surgical tape extended around the patient's chin and secured to the operating table to hold the patient's head in the correct position, this method is unreliable and inadequate. Because the tape is attached to the table at a point lower than the chin, it is impossible to pull the chin up by this method. Furthermore, the tape can slip or detach from either the patient's chin or the operating table and can even tear the patient's skin. Also, surgical tape can irritate sensitive facial tissues of the patient.

So-called chin props, which comprise a ball on the end of an arm supported from the operating table, have also been used to maintain a patient's airway open during surgery. The ball engages under the patient's jaw and provides a force to tilt the patient's head. However, these devices, if misapplied, can constrict the airway somewhat by pressing the patient's tongue through the soft tissue under the jaw. Pressure applied directly to the point of the jaw at the patient's chin is much more effective for maintaining the airway open. Also, existing chin props are large and cumbersome, and they may get in the way of surgeons operating on the patient.

It is apparent, therefore, that a need exists for improved equipment and procedures for maintaining an anesthetized surgical patient's airway in a suitably open state. To be effective, the procedure should be simple and reliable, and the equipment should be easy to use, reliable, and non-irritating to a patient's skin. Once fitted to the patient's needs and circumstances, the equipment should free the anesthetist's hands for other tasks. Also, the equipment should be capable of being adjusted readily on the patient. The equipment, when engaged with a patient's head, should not interfere with the use of anaesthesia masks in the vicinity of a patient's mouth. Such equipment can reduce the need for use of endotracheal tubes.

SUMMARY OF THE INVENTION

This invention effectively addresses the need which has been identified above. The invention provides simple, effective and reliable procedures and devices which enable a force of desired magnitude to be applied in a desired direction to a patient's chin to hold the patient's head in a position which produces an open airway. The equipment provided by the invention can be installed quickly by an anesthetist between an operating table and an anesthetized patient's head to provide the desired head positioning function independently of the anaesthetist who normally is positioned adjacent the patient's head during surgery.

Generally speaking, a chin support apparatus is useful for holding an anesthetized patient's head in a way that keeps the patient's airway open. A pylon is releasably connected to an operating table and extends substantially vertically from the table. A tether engages the patient's head at one end and the pylon at the other end to apply a force to the patient's chin to keep the airway open.

In a preferred embodiment of the invention, a chin support at the head of an operating table comprises a pylon extending upward from the table and a tether attached to its upper end. The tether extends around an anesthetized patient's chin in order to tilt the patient's head and maintain an open airway while the patient is unconscious during surgery. The pylon attaches to the operating table by use of a J-shaped bracket. Tension applied to the tether holds the bracket securely in place relative to the operating table.

An advantage of the present invention is that the anesthetist is not required to physically hold the patient's head to maintain the proper airway. This allows the anesthetist to use both hands during the surgery so that various other functions can be performed in confidence knowing that the patient's airway is being securely held open.

A further advantage of the present invention is that the device can be fabricated with no moving parts, yet it can be securely and easily attached to the operating table using the tension on the tether to hold it in place. Adjustable mounting means can be provided for the pylon so that it can be attached securely to virtually any operating room table.

Furthermore, by applying tension from a point higher than the patient's chin, the chin can be pulled in an upward direction which is much more effective at keeping the airway open than tension applied from a point at the surface of the operating table.

A still further advantage of the present invention is that its simple and compact construction allows for easy cleaning and sterilization so that it can be reused.

BRIEF DESCRIPTION OF THE DRAWINGS

The above-mentioned and other features and advantages of the invention are more fully set forth in the following description of the presently preferred and other embodiments of the structural and procedural aspects of the invention. That description is presented with reference to the accompanying drawings, wherein.

DETAILED DESCRIPTION OF THE INVENTION

Figure 1:
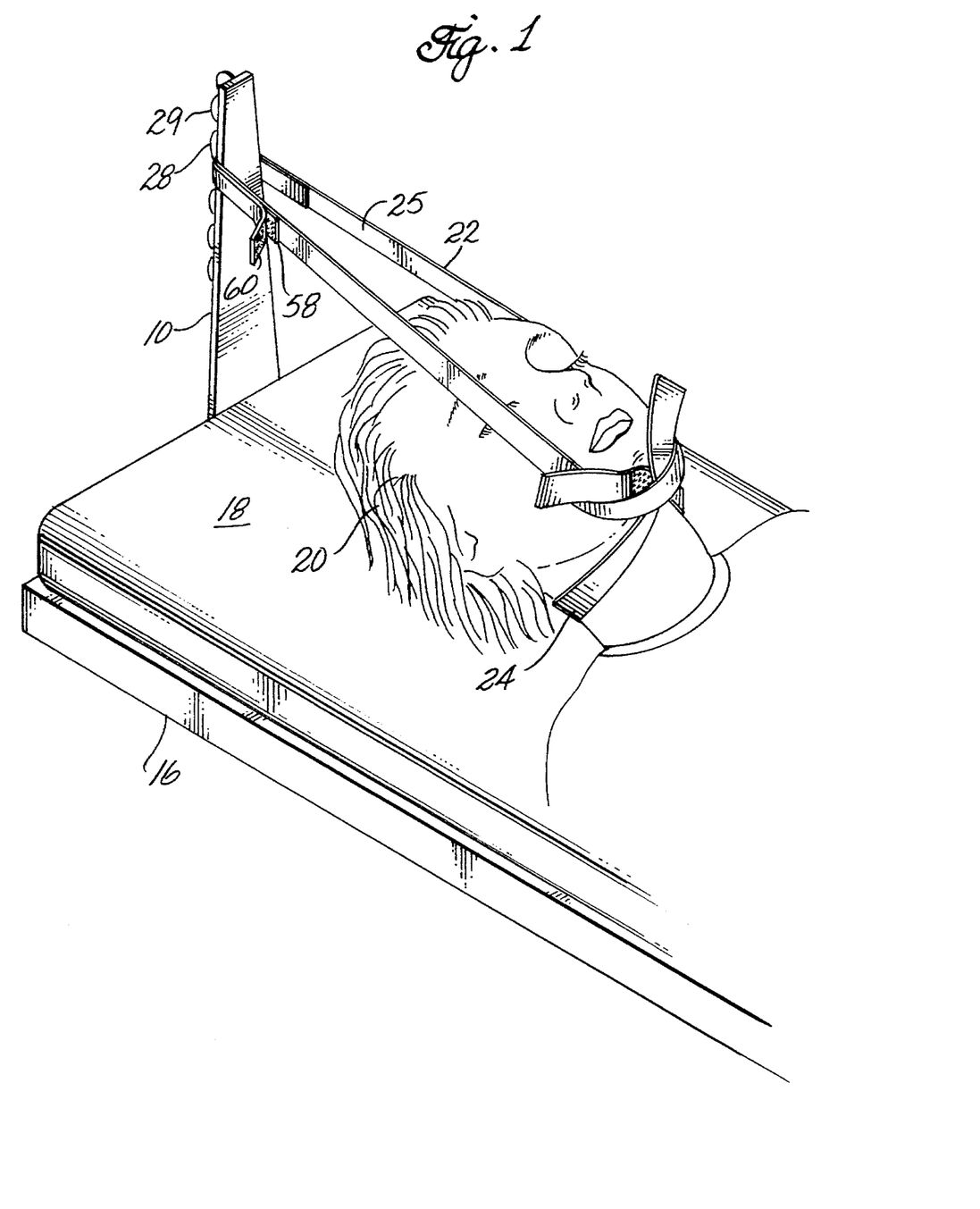
FIG. 1 is a perspective view of the chin support device in use with a patient in a supine position on an operating table.
Figure 2:
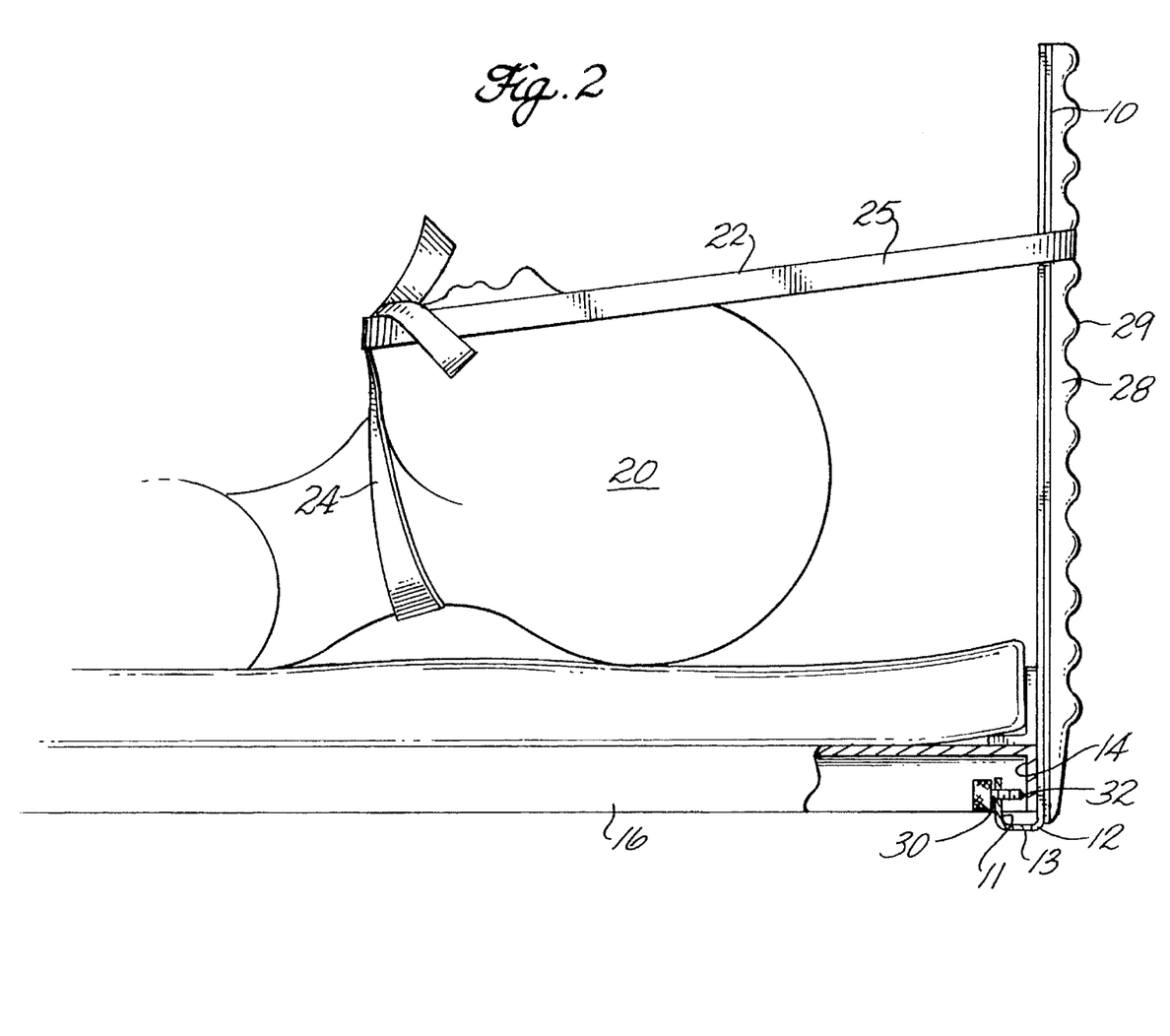
FIG. 2 is a side view, partially in cross-section, of the chin support device in use in the context shown in FIG. 1.

Referring to the drawings, there is shown in FIGS. 1 and 2 a chin support device being used to maintain an unconscious patient's airway open during surgery. The chin support device comprises a pylon 10 and a tether 22. The pylon has a J-shaped bracket 12 at its lower end by which the pylon is coupled to a depending flange 14 at the head end of an operating table 16. The operating table additionally includes a foam pad 18 for the comfort of the patient. A patient is anesthetized and rests in a supine position on the operating table.

The patient's head 20 is maintained in a chin-up tilted position by tether 22 so as to keep the patient's airway open during the surgery. The tether preferably comprises two straps. A neck strap 24 wraps around the patient's neck and fastens to itself preferably at the point of the patient's chin. A chin strap 25 fastens to the neck strap at the patient's chin and extends to the pylon. The chin strap is optimally connected to the pylon at a point high enough on the pylon above the operating table to lift the chin in an upward direction. The neck strap keeps the chin strap from slipping from the patient's chin while the chin strap applies an appropriate force in a desired direction to keep the patient's airway open.

This arrangement of the tether is extremely effective and versatile. Because the chin strap extends along the sides of the patient's face, the patient's nose and mouth are unobstructed, thus allowing the use of face masks without interference with the tether. Furthermore, the chin strap can be readily and easily adjusted during the surgery without removal of any face mask or tubes that may be in use.

Because the chin strap is designed to apply pressure at the patient's chin, the patient's head can be maintained in a proper position without applying pressure to the tongue which can interfere with the airway. This is especially useful for patients who are in a supine position on the operating table.

While the tether is described as preferably comprising two separate straps, a single strap could be used to extend around the patient's neck, fasten upon itself at the patient's chin and extend along the sides of the patient's head, around the pylon and fasten upon itself again in a figure-eight arrangement.

The pylon 10 is defined so that it can be used with operating tables having end rails and also with operating tables having no end rails. To that end, a stop flange 26 extends laterally from a forward face of the pylon, at a location on the pylon near its lower end, towards the operating table so as to prevent the pylon from slipping in a downward direction which would disengage the bracket 12 from flange 14 of the operating table in the case where the pylon is used with a table having no end rail. In the preferred embodiment of the invention, the bracket includes means for adjusting the bracket to fit various different operating table configurations. In FIG. 2, the adjusting means includes a shaft 30 that is threaded through a hole in a leg 11 which extends upwardly from a return bend 13 at the lower end of pylon 10. The leg 11 is substantially parallel to the pylon adjacent its forward face and is defined to lie on the side of table flange 14 opposite the pylon with the upper end of leg 11 above the lower edge of flange 14 when stop flange 26 engages the top of the table (see FIG. 2). The shaft includes a tip 32 that engages to the inside face of the operating table flange to hold the pylon in place. A knurled head 34 on the shaft allows simple hand adjustment of the shaft.

The pylon can further include a rib 28 running along its length normal to the plane of the generally flat pylon. The rib stiffens the pylon against bending in response to loads applied to the pylon by chin strap 25. Scallops 29 along the length of the rib help hold the tether in place on the pylon by preventing the chin strap from moving along the length of the pylon after the chin strap has been secured in position between the patient's chin and the pylon.

Figure 2A:
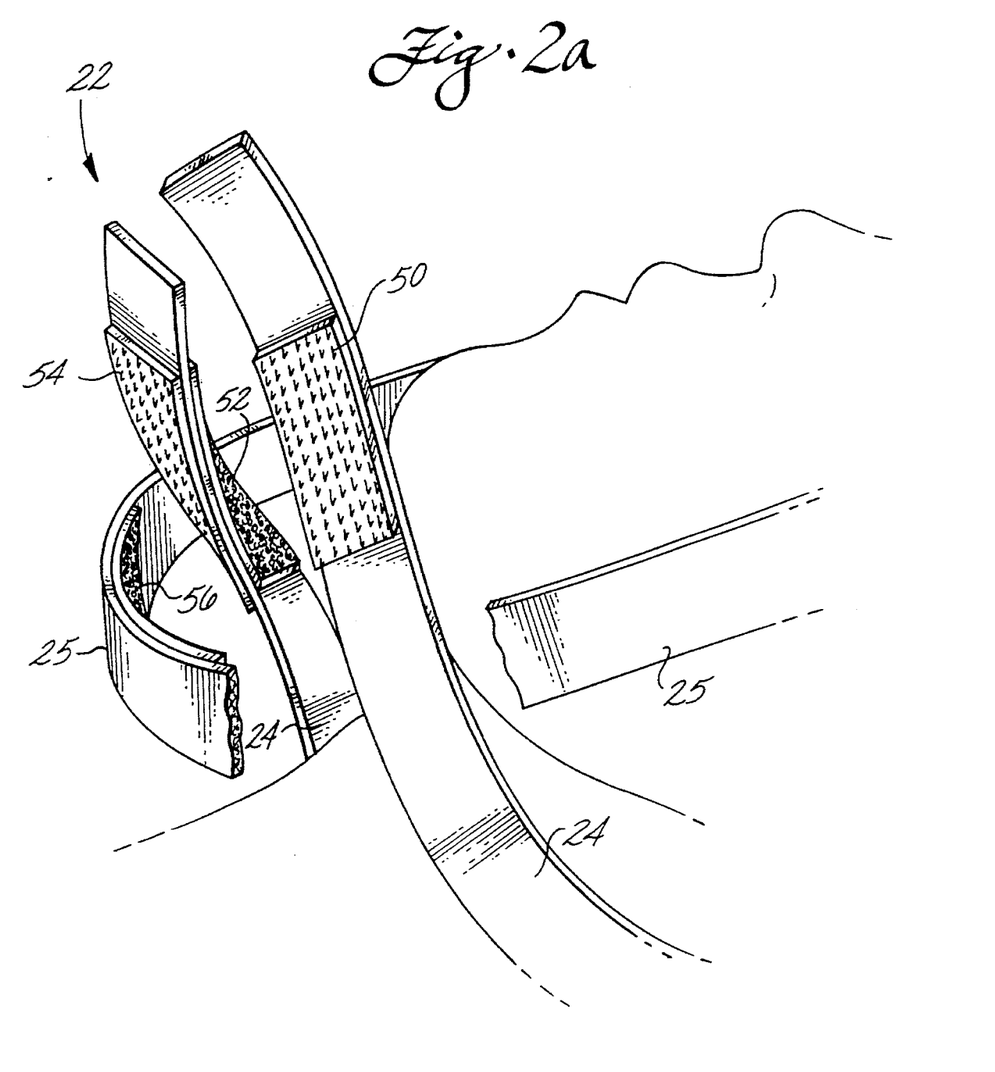
FIG. 2a is an enlarged fragmentary elevation view showing the relation of tether components to each other at the point of a patient's chin in use of a presently preferred tether.

In the presently preferred embodiment of the invention, the components of the tether arrangement include hook and pile fasteners such as are known under the trademark VELCRO. FIG. 2a is an enlarged fragmentary view of the tether showing how the neck and chin straps 24 and 25 are fastened at the patient's chin. Neck strap 24 has a first layer of hook fabric 50 at one end on the side of the strap opposite the point where it contacts the patient's chin. The other end of the neck strap extends around the patient's neck and a first layer of pile fabric 52, carried on one side of the chin strap, fastens to the first layer of hook fabric at the patient's chin. On the other side of the chin strap, opposite pile fabric 52 on the neck strap, is a second layer of hook fabric 54.

A second layer of pile fabric 56 is found on the chin strap 25, preferably at about the midlength of the chin strap, and fastens to the second layer of hook fabric 54 on the neck strap. The ends of the chin strap extend along the sides of the patient's head and around pylon 10 (FIG. 1). The ends of the chin strap are fastened to one another at hook fastener 58 and pile fastener 60, as shown in FIG. 1.

The various layers of hook fabric and pile fabric preferably extend over a sufficient portion of the length of each strap so that the straps can be broadly adjusted for various patients in various positions on the operating table. It should be apparent that straps having one continuous layer of pile fabric on one side and another continuous layer of hook fabric on the other side will allow a very broad range of adjustment. However, if continuous layers of hook and pile fabric are used, the straps should be used in such a way that the pile fabric is in contact with the patient's skin rather than the hook fabric in order to avoid unnecessary abrasions to the patient's neck, chin and face.

Figure 3:
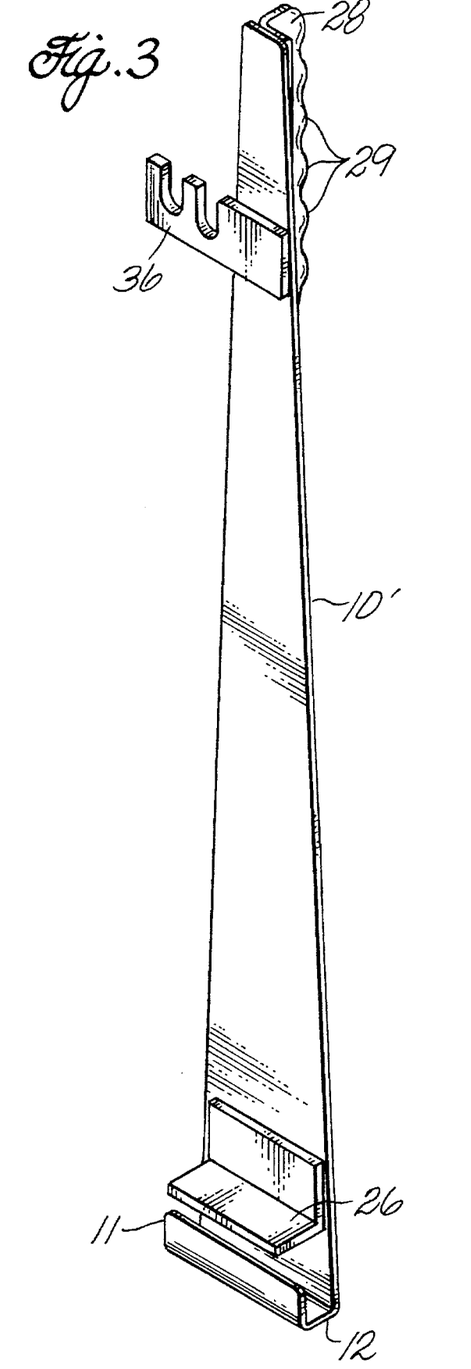
FIG. 3 is a perspective view of another embodiment of a pylon useful in the practice of the invention.

Referring now to FIG. 3, another pylon 10' is shown. Pylon 10' includes bracket 12, stop flange 26, rib 28 and scallops 29 as described above. Pylon 10' further includes an optional notched arm 36 over which tubes, such as are used in administering anesthesia to the patient, can be draped. It should be noted that this embodiment of the pylon does not include an adjustable bracket. Instead, the bracket is held in engagement with the flange of the operating table by the tension on the tether when it is attached to the patient's chin. By applying tension to the tether, the top of the pylon is pulled toward the center of the operating table. This in turn causes the lower part of the bracket to pull outwardly away from the operating table to firmly engage the bracket leg 11 to the flange of the operating table.

Figure 4:
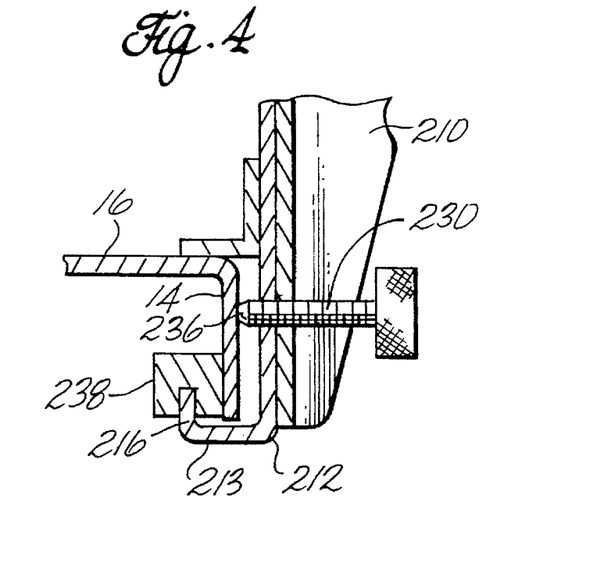
FIG. 4 is a fragmentary side elevation view, partially in cross-section, showing an arrangement for coupling a pylon to an operating table having no end rail.
Figure 5:
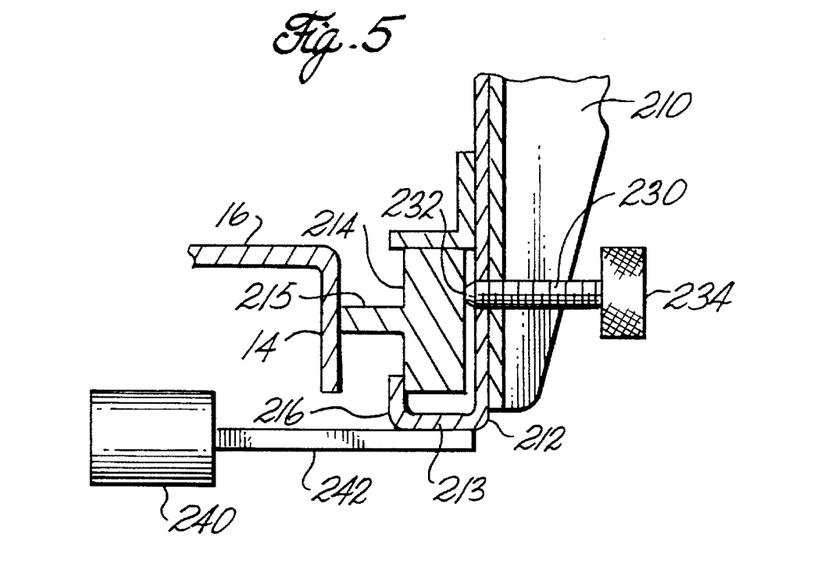
FIG. 5 is a fragmentary side elevation view, partially in cross-section, of an arrangement for coupling the same pylon as shown in FIG. 4 to an operating table having an end rail.

Referring now to FIGS. 4 and 5, another embodiment of the pylon lower end bracket is shown. Pylon 210 has a J-shaped bracket 212 that fits loosely to an operating table. FIG. 4 shows an operating table 16 of the type having a flange 14 extending around its perimeter. FIG. 5 shows an operating table 16 that has a rail 214 carried at its head end on spacers 215. The rail is mounted to table flange 14 in spaced relation from the table flange. The bracket of pylon 210 fits around this rail.

The embodiment of the invention shown in FIGS. 4 and 5 includes adjustable means for securing the bracket to either the table flange 14, or to the rail 214 of the operating table. The adjustable means includes a shaft 230 that is threaded through a hole in the bracket, namely, through the lower end of the pylon above the return bend 213 to leg 216 which lies adjacent the lower margin of the pylon forward face. The threaded hole is located at the portion of the J-bracket 212 that is outside the flange of the operating table. In the embodiment shown in FIG. 4, shaft 230 is threaded through the hole and has a tip 232 which engages with the outside of table flange 14. Head 234 of the shaft allows the shaft to be tightened. A knurled knob is preferred so that tools are not needed for tightening the shaft. This embodiment also includes a slotted adapter block 238 which allows a pylon designed for an operating table with a rail 214 to be fitted to an operating table with a flange 14.

In the installation shown in FIG. 5, shaft 230 is threaded through the hole and tip 232 engages with the outside of rail 214. As with the installation of FIG. 4, knurled knob 234 allows simple adjustment of the shaft. FIG. 5 also shows an optional counterweight 240 at the end of extension arm 242 that is attached to the bottom of the J-bracket. The counterweight causes the pylon always to tend to tip toward the table and prevents it from falling off the table rail, even if the adjustable bracket is loose.

Figure 6:
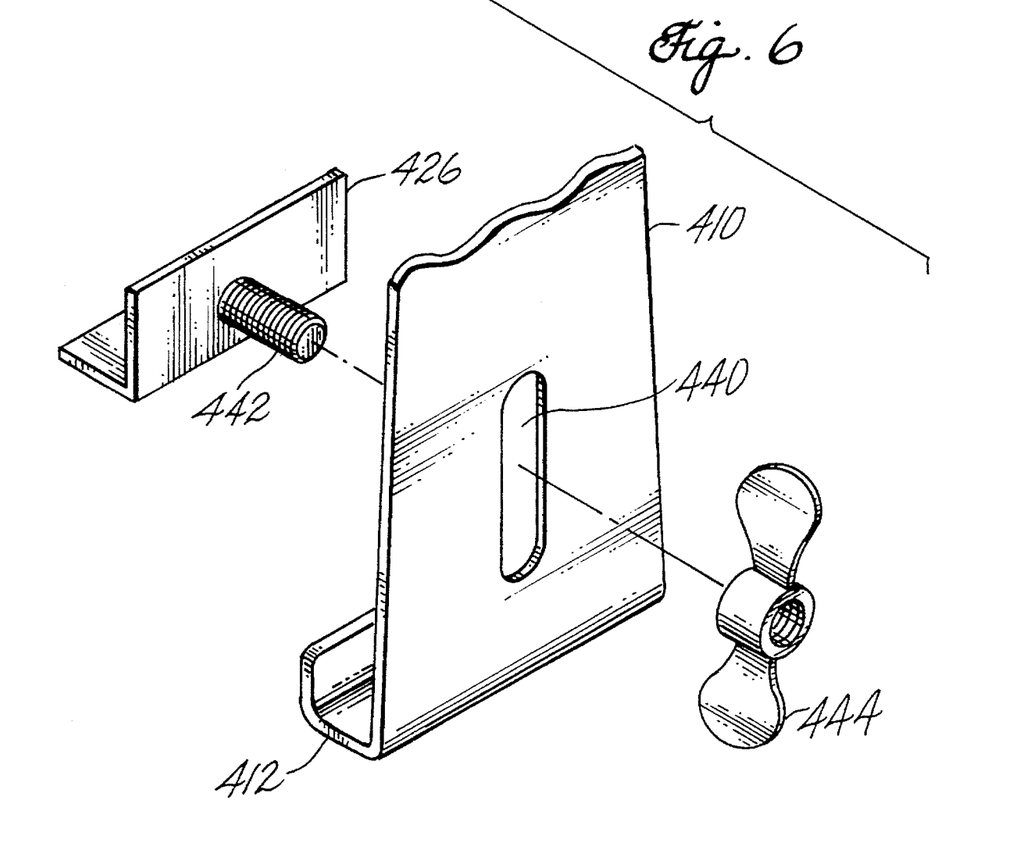
FIG. 6 is an exploded fragmentary perspective view of another embodiment of a pylon bracket.

Another embodiment of the invention is shown in FIG. 6. Pylon 410 has a J-shaped bracket 412 that fits around a flange or a rail of the operating table. This embodiment further includes an adjustable stop flange 426. The pylon has a slot 440 that extends along a portion of the length of the pylon. A threaded stud 442 on the stop flange extends through the slot and is secured to the pylon with wing nut 444. The stop can be raised or lowered to accommodate virtually any size or configuration of operating table.

Figure 7:
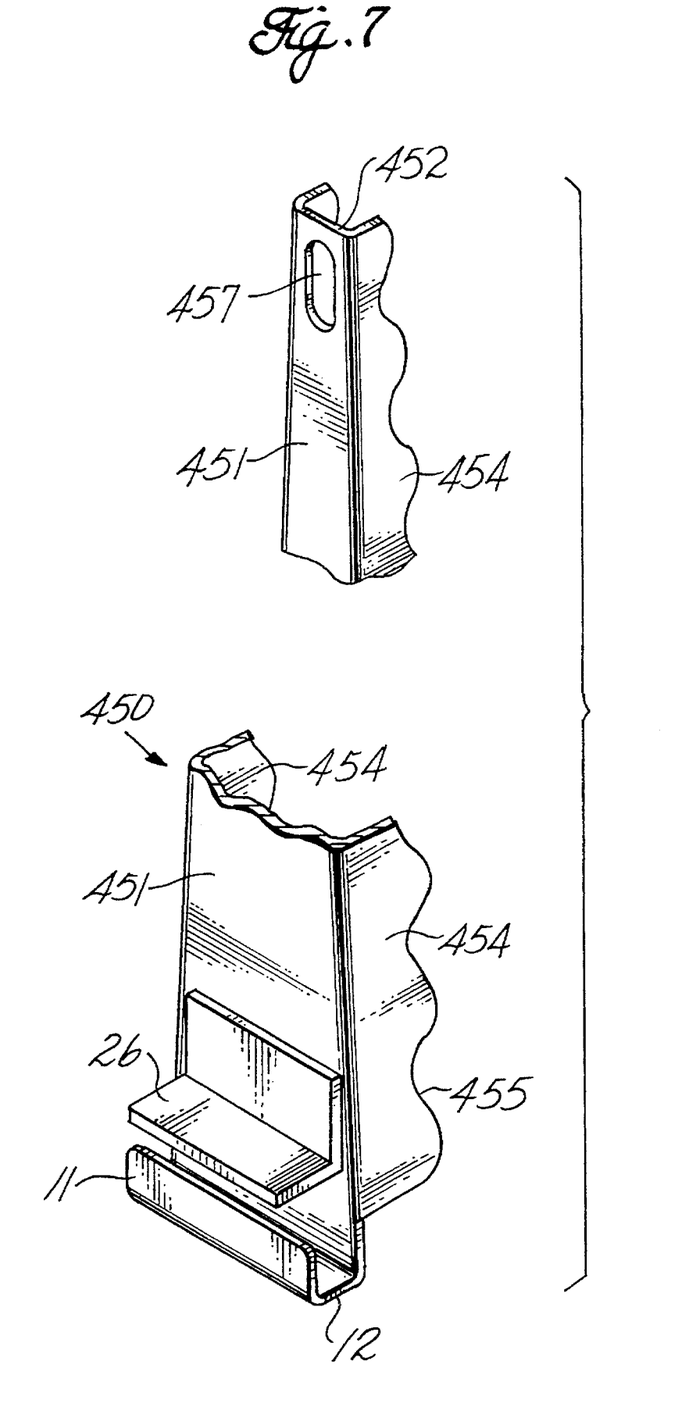
FIG. 7 is a fragmentary perspective view of another form of pylon.

Another pylon structure 450 according to this invention is shown in FIG. 7. Pylon 450 can be structured at its lower end in the manner of pylon 10' or, if desired, in the manner of the lower ends of the pylon described above. Pylon 450 has an elongate upwardly extending body 451 which preferably decreases linearly in width proceeding upwardly along the pylon to its upper end 452. The body is stiffened against bending by ribs 454 which extend rearwardly from the body along each of the vertical edges of the body. The ribs preferably are formed integral with the body and comprise flanges of the body. The depth of the ribs, i.e., their dimension perpendicular to the body, preferably increases proceeding downwardly along the body. The rear edges of the ribs can be scalloped, as at 455, for the reasons described above. A hole 457 can be formed through the pylon body 451 near its upper end to enable the pylon to be stored, when not in use, on a hook on the anesthetist's anesthesia machine.

Figure 8:
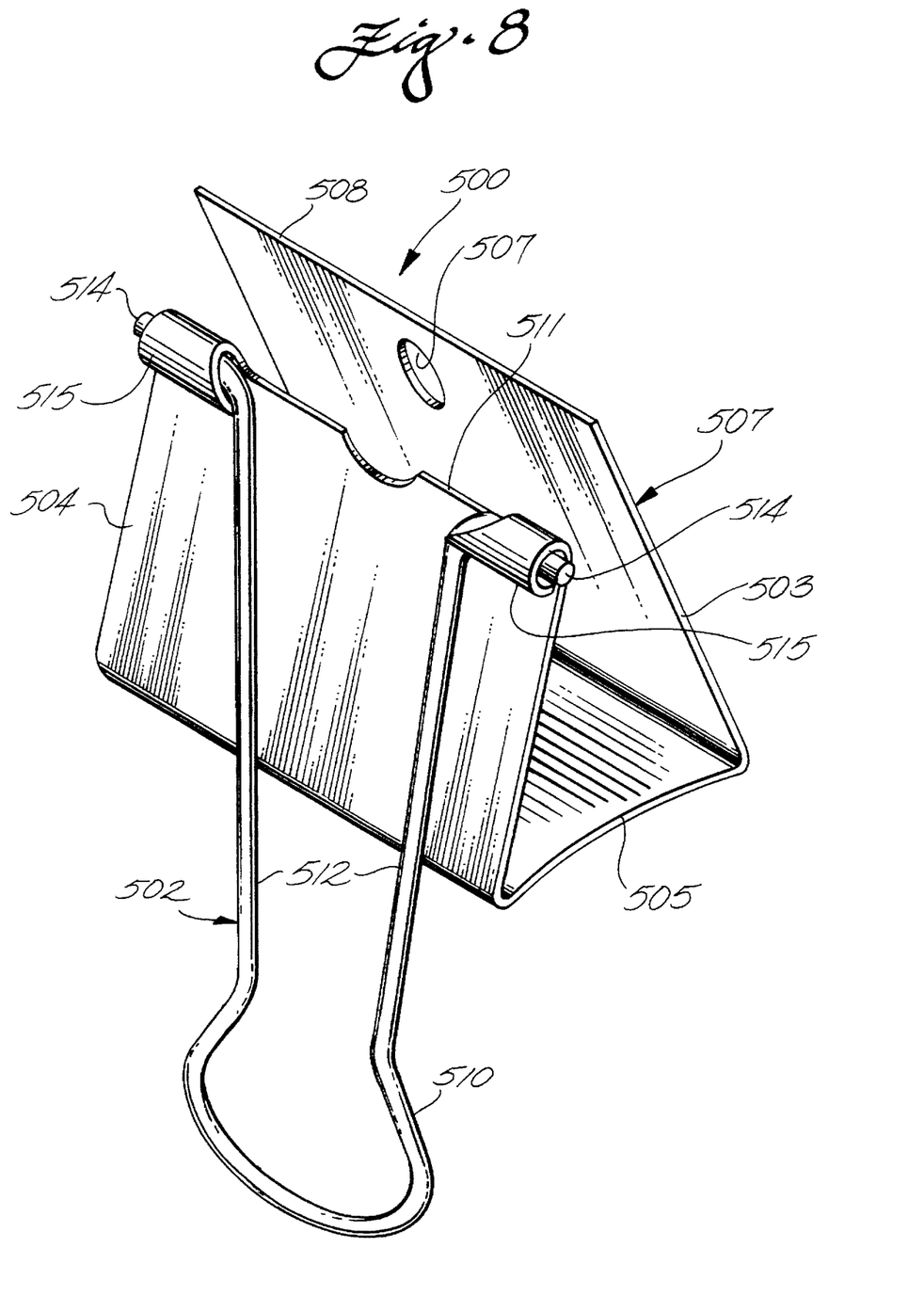
FIG. 8 is a perspective view of a resilient clip assembly useful for mounting the pylon of FIGS. 4 and 5, for example, to an operating table.
Figure 9:
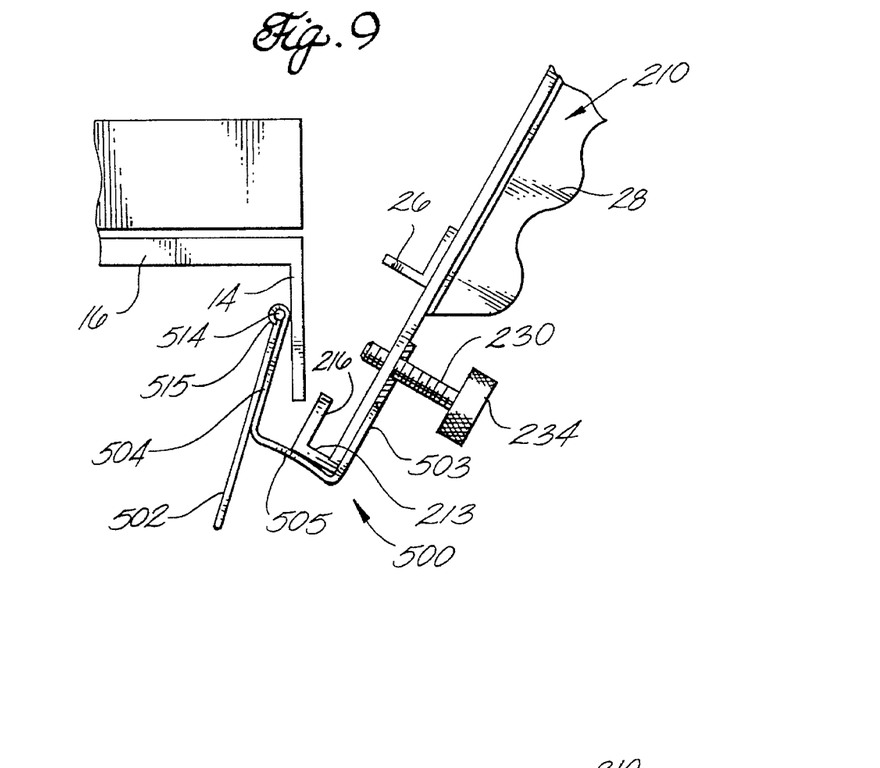
FIG. 9 is a fragmentary elevation view showing a step in the mounting of the pylon to a table by use of the clip assembly shown in FIG. 8.
Figure 10:
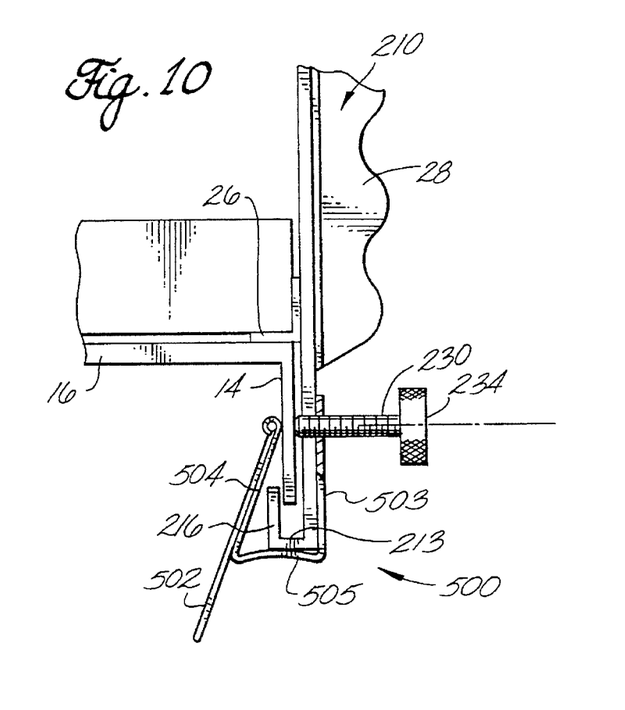
FIG. 10 is a view similar to that of FIG. 9 showing the pylon and clip assembly as mounted to the table.

FIG. 8 is a perspective view of a resilient clip assembly 500 which provides a convenient and effective way to mount pylon 201, for example, to a wide range of a operating table edge constructions. The clip assembly preferably is composed of two parts, namely, a resilient member 501 and a bail-like operating lever 502 which preferably is hingedly and removeably connected to member 501. The resilient member 501 conveniently is fabricated from a relatively thin piece of spring steel of selected width and length, which piece is bent transversely of its length into a return-bend or U-shaped configuration having opposed base and moveable legs 503 and 504, respectively, which are connected by a central connecting portion 505 in an integral manner. The leg 503 is called a base leg because in use it bears against the face of the pylon 210 which is opposite from operating table 16 and is effectively fixed on the pylon. Leg 504 is moved relative to leg 503, to install the pylon on the table, against the inherent resilience of member 501 which flexes principally in its connecting portion. Such movement of leg 504 is produced by use of lever 502 which pivots about a fulcrum defined by a lower edge of leg 504 to move the upper end of leg 504 away from let 503, thereby to open the clip assembly so that it and the pylon can be connected to a suitable table edge feature such as is shown in FIGS. 9 and 10.

A hole 507 is formed through leg 503 centrally of its width near an upper edge 508 of the leg. As shown in FIGS. 9 and 10, hole 507 accommodates the threaded shaft 230 of adjustment knob 234 which serves to position the clip assembly on the pylon in cooperation with the clearance fit (see FIG. 10, e.g.) of the bend 213 and leg 216 of the pylon into the inside of the clip assembly in the return-bend portion of member 501.

Lever 502 conveniently is made of a length of heavy gauge wire 510 which is bent into a substantially U-shaped configuration which has legs 512 longer (preferably about two times longer) than the extent of the clip assembly's movable leg 504 between its upper edge 511 and connecting portion 505. Coaxially aligned, outwardly turned terminal portions 514 at the free ends of legs 512 form hinge axles which are received in and turn in hinge sleeves 515 formed by member leg 504 at its upper edge as shown in FIG. 8.

The clip assembly 500 is readily disconnectible from the pylon, and lever 502 is readily disassemblable from spring member 501, for disinfecting and sterilizing all parts between uses of the pylon and the clip assembly.

The similarities between the clip assembly shown in FIG. 8 and a common form of office spring clip will be apparent, as will the manner in which the clip assembly is used. FIG. 9 shows a step in the application of the pylon to a flanged edge 14 of operating table 16, via use of clip assembly 500. FIG. 10 shows the clip assembly holding the pylon on the table in such a manner that operation of knob 234 produces movement of the upper end of the pylon toward and away from the central area of the table.

The normal condition of the clip assembly is one in which edge 511 of leg 504 bears forcefully against the adjacent face of leg 503 due to a spring load created by deflection of the connecting portion 505 of the clip assembly.

It will be apparent that clip assembly 500 is used best with a pylon which has the lower end of its rib 28 terminated sufficiently far above the lower end of the pylon that leg 503 of the clip assembly can lie flat against the lower end of the back face of the pylon, as shown in FIG. 9 and 10.

It should be noted that the embodiments shown and described are just a few examples of the various forms which the invention may take. Variations or combinations of the arrangements described above are possible.

In the preferred embodiment of the present invention, the pylon is made of material such as stainless steel which can be easily cleaned and sterilized so that the device can be reused. The tether preferably is made of a durable material that can be sterilized yet is capable of quick adjustment. Hook and pile fabric connectors have been described in the preferred embodiment; however, other fasteners such as snaps or even adhesive tape could be used. The tether and its straps could also be made of a disposable material.

Furthermore, the invention has been described for use on a patient in a supine position on the operating table. However, the invention can also be effectively used for patients who are on their sides, or even those who are prone on the operating table.

What is claimed:

1. A pylon connectible to a selected structural feature at a perimeter of a surgical operating table, the pylon comprising an elongate, substantially rigid pylon member having upper and lower ends, the pylon member having at its lower end mounting means releasably cooperable with the table perimeter feature for holding the pylon member on the table in a substantially vertical attitude in which the pylon member is constrained from rotation toward the table, the mounting means including adjustment means operable for controlled rotation of the pylon member away from the table.

2. The pylon of claim 1, additionally comprising a rib running substantially the length of the pylon member for stiffening the pylon member against bending.

3. The pylon of claim 2, additionally comprising scallops along the rib.

4. The pylon of claim 1 wherein the mounting means comprises:

a J-shaped bracket for releasably engaging the perimeter feature of the operating table; and a stop for releasably engaging the top of the operating table for preventing the bracket from moving out of engagement with the perimeter feature of the operating table.

5. The pylon of claim 4, wherein the stop is adjustably positionable on the pylon member.

6. The pylon of claim 5, further comprising:

a slot defined by the pylon member and extending along a portion of the lower end thereof in a lengthwise direction;

a threaded member on the stop which fits through the slot; and a nut threaded to the threaded member for holding the stop to the pylon member.

7. The pylon of claim 4, wherein the bracket further comprises a shaft threaded through a hole in the bracket, the shaft having a tip for engaging against the perimeter feature of the operating table and a head for tightening or loosening the shaft.

8. The pylon of claim 4 wherein the mounting means further includes an adapter block for engaging with the bracket to releasably engage a second operating table with a different perimeter feature.

9. The pylon of claim 1 further comprising:

an arm extending from the lower end of the pylon member in a substantially horizonal direction toward the operating table; and a counterweight carried in a spaced relationship from the lower end of the pylon member by the arm.

10. The pylon of claim 1 further comprising an arm extending from the pylon member for holding a plurality of tubes.

11. The pylon of claim 1 wherein the mounting means includes spring means for resiliently clamping the pylon member to the table perimeter feature.

12. The pylon according to claim 11 wherein the spring means includes a U-shaped resilient member having opposed legs biased to contact each other at a free end of one of the legs, and means for mounting one of the legs to a lower end portion of the pylon member.

13. The pylon according to claim 12 wherein the mounting means includes an actuator lever connected to one of the legs of the resilient member operable for moving that leg against said bias away from the other leg.

* * * * *